(12) United States Patent
Bogie et al.

(10) Patent No.: US 10,201,703 B2
(45) Date of Patent: Feb. 12, 2019

(54) INTEGRATED SURFACE STIMULATION DEVICE FOR WOUND THERAPY AND INFECTION CONTROL

(71) Applicants: The United States of America, as represented by the Department of Veterans Affairs, Washington, DC (US); Case Western Reserve University, Cleveland, OH (US)

(72) Inventors: Kath M. Bogie, Shaker Heights, OH (US); Steven L. Garverick, Cleveland Heights, OH (US); Christian A. Zorman, Euclid, OH (US); Daniel S. Howe, San Diego, CA (US)

(73) Assignees: The United States of America, as represented by the Department of Veterans Affairs, Washington, DC (US); Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/675,270

(22) Filed: Mar. 31, 2015

(65) Prior Publication Data

US 2016/0287868 A1 Oct. 6, 2016
US 2018/0369582 A9 Dec. 27, 2018

Related U.S. Application Data

(63) Continuation of application No. 14/363,277, filed as application No. PCT/US2013/022139 on Jan. 18, 2013, now Pat. No. 9,320,907.
(Continued)

(51) Int. Cl.
| | |
|---|---|
| *A61B 5/0476* | (2006.01) |
| *A61N 1/36* | (2006.01) |
| *A61N 1/04* | (2006.01) |
| *B29K 79/00* | (2006.01) |
| *B29K 105/16* | (2006.01) |

(Continued)

(52) U.S. Cl.
CPC ....... *A61N 1/36014* (2013.01); *A61N 1/0468* (2013.01); *A61N 1/0472* (2013.01);
(Continued)

(58) Field of Classification Search
CPC .......... A61B 5/6833; A61B 2560/0412; A61N 1/0472; B29K 2079/08; B29K 2995/0005
See application file for complete search history.

(56) References Cited

U.S. PATENT DOCUMENTS

| | | | |
|---|---|---|---|
| 7,970,450 B2 * | 6/2011 | Kroecker | A61B 5/0006 600/391 |
| 2010/0241057 A1 * | 9/2010 | Pak | A61N 1/044 604/20 |

OTHER PUBLICATIONS

Wound EL (Mölnlycke Health Care) Non patent literature/product, accessed on May 1, 2015: @ http://www.molnlycke.com/advanced-wound-care-systems/electrical-stimulation/#confirm.
(Continued)

*Primary Examiner* — Michael D Abreu
(74) *Attorney, Agent, or Firm* — Ballard Spahr LLP

(57) ABSTRACT

The present invention provides a thin and flexible device and method of use thereof for wound treatment and infection control. The integrated surface stimulation device may comprise a complete wireless stimulation system in a disposable and/or reusable flexible device for widespread use in multiple therapeutic applications. The invention would be situated on the skin surface of a patient and would be activated so as to reduce the overall occurrence of infections and/or increase wound healing rates. As provided, the device will comprise an integrated power supply and pre-programmable stimulator/control system on a flexible polymeric substrate layer with areas of stimulating electrodes, applied using techniques such as those found in additive manufacturing processes. The device is especially valuable in treating biofilm-based infections.

12 Claims, 5 Drawing Sheets

Related U.S. Application Data

(60) Provisional application No. 61/594,105, filed on Feb. 2, 2012.

(51) Int. Cl.
*B29K 505/14* (2006.01)
*B29L 31/00* (2006.01)
*B33Y 10/00* (2015.01)
*B33Y 50/02* (2015.01)
*B33Y 80/00* (2015.01)
*B29C 64/135* (2017.01)
*B29C 64/386* (2017.01)

(52) U.S. Cl.
CPC .......... *B29C 64/135* (2017.08); *B29C 64/386* (2017.08); *B29K 2079/08* (2013.01); *B29K 2105/16* (2013.01); *B29K 2505/14* (2013.01); *B29K 2995/0005* (2013.01); *B29L 2031/753* (2013.01); *B33Y 10/00* (2014.12); *B33Y 50/02* (2014.12); *B33Y 80/00* (2014.12)

(56) References Cited

OTHER PUBLICATIONS

Various Devices, Including GV350 model (Biomedical Life Systems) Non patent literature/product, accessed on May 1, 2015.
POSiFECT(Biofisica) Non patent literature/product, accessed on May 1, 2015: @ http://www.wounds-uk.com/journal-articles/bio-electrical-stimulation-therapy-using-posifectrd.
Procellera Wound Dressing Non patent literature/product, accessed on May 1, 2015: @ http://procellera.com/procellera/technology.

* cited by examiner

Fabrication sequence with a polyimide substrate

☐ Si     ▦ polyimide     ▨ photoresist     ▧ Pt     ▥ Cr

INTEGRATED SURFACE STIMULATION DEVICE FOR WOUND THERAPY AND INFECTION CONTROL

This application claims priority to U.S. non-provisional patent application Ser. No. 14/363,277, filed on Jun. 5, 2014, which is a U.S. National Stage filing under 35 USC 371 of, and in turn claims priority from, PCT Application No. PCT/US13/22139, filed on Jan. 18, 2013, which in turn claims priority from U.S. provisional Patent Application No. 61/594,105, filed on Feb. 2, 2012, the contents of which are each hereby incorporated by reference in the entirety.

FIELD OF THE INVENTION

The present invention relates to medical devices that utilize electrical stimulation for surface-stimulated treatment of infections and wounds in the human body. The present invention is a patch, i.e. a thin, partially or fully flexible covering, which incorporates a stimulation controller, wireless communication device, miniaturized or wireless power, and a substrate with customizable treatment electrodes.

Open wounds can be difficult to treat. In particular, chronic wounds, such as ischemic wounds and pressure ulcers, are a major clinical challenge in the long-term care of people with physical impairment and/or disability. Even in mild cases, special care is required. Scientific studies show that electrical stimulation quickens wound healing, reduces scar formation, and can reduce discomfort therefrom. For example, galvanic treatment has been known for many years as a means to deliver drugs and cosmetic active agents into the skin for therapeutic purposes. Such approaches are based on mechanisms such as iontophoresis and electro-osmosis. A review of the literature reveals that galvanic treatment is also valuable in the treatment of wounds and scars, via several modes of action including accelerated cell regeneration; tissue repair; accelerated cutaneous barrier recovery (even with very low current); improved blood circulation; improved respiration; and scar reduction. However, to date electrotherapy protocol has been quite lacking especially for problematic wounds such as pressure ulcers, and furthermore, its use in corollary conditions, such as infections is essentially unknown.

To this end, there is a recognized need for an improved integrated surface stimulation device (ISSD) that can be used in a variety of mobile care settings, from the intensive care unit to the patient's home. It would be highly advantageous for this ISSD to employ electrical stimulation for wound treatment and/or infection control, embodied on a thin and flexible substrate that includes a self-contained power source and controller. Preferably, such a system and device should be disposable and customizable for particular types of wounds and infection associated therewith, including the treatment protocol itself. Additional benefits may be recognized when such a device may be fabricated according to novel additive manufacturing techniques, and when provided with advanced power sources, such as Lithium polymer batteries or the like that provide sufficient power in order to deliver reliable stimulation to a large wound for an extended period of time. Further benefits can be realized when the novel application of the innovative techniques and apparatus is used in order to effectively treat infected wounds, especially those with biofilm colonies.

SUMMARY OF THE INVENTION

The present invention relates to a novel approach to improving the management of infection and wound healing through the use of an integrated surface stimulation device (ISSD). The ISSD for wound management and infection control, according to the present invention, is a wearable, flexible adhesive electrical stimulation patch that is wireless, with the totality of the component electronics and power source being wholly encapsulated thereon in a thin, flat instantiation. In providing the above, the invention utilizes advanced materials and fabrication techniques, and is designed so as to have a simple, user-friendly communication interface. More specifically, one embodiment of the invention contains all the components of a single-channel, current-controlled stimulation system within a lightweight, flexible, independently-powered portable device utilizing a custom, miniaturized (approximately 2-9 mm$^2$) Application-Specific Integrated Circuit (ASIC), also known as a custom IC. The ISSD uses advanced materials and cutting-edge fabrication techniques to provide sustained or intermittent application of Electrical Stimulation (ES) combined with maintenance of a stable wound healing environment. An optional software package with a graphical user interface (GUI) may also be provided for use on a partner device connected to the invented device, to be employed by a medical professional.

The ISSD comprises a complete wireless stimulation system in a disposable and/or reusable flexible device for widespread use in multiple therapeutic applications. The invented device would be situated on the skin surface of a patient and would be activated so as to reduce the overall occurrence of infections and/or increase wound healing rates. As manufactured, the device will comprise an integrated power supply and pre-programmable stimulator/control system mounted on the upper face of a flexible polymeric 'backbone' or substrate layer. The lower face of the substrate layer will comprise areas of stimulating electrodes, applied using thin film deposition techniques such as sputtering, evaporation, electroplating, and spray coating or foil deposition. Alternatively the substrate layer may be constructed using additive manufacturing techniques (one variant of which is known as 3D printing in some applications), whereby interconnection means prepared thereon exist for connection between components of circuitry and include vias that are constructed and filled in a single process. The advantage of additive manufacture of the substrate as disclosed herein is that this approach would enable building the substrate in a single process using multiple materials, thereby eliminating the need for a mask (hereafter occasionally referred to as a "maskless fabrication" of the substrate with electrodes), and further to this point, the same may be customized in a dramatically easier fashion than if produced according to the other embodiments of manufacturing as referenced above. Such maskless fabrication techniques, vary, but in one illustrative embodiment, may comprise additive manufacturing approaches such as selective laser melting, where successive layers of material powder are exposed so as to be melted or heated with a laser or ion beam, thereby hardening only certain portions in order to produce the desired final structure. Further to this, the equipment may be machines such as the Envisiontec Bioplotter™, although many other machines may be utilized as can be readily appreciated. The non-conductive materials may be polyamide, silicone or other flexible polymeric materials. The conductive materials may by silver particles in a binder material, platinum particles in a binder material, conductive inks or other conductive polymeric material. When provided in accordance with the above, the device can then be applied to the user with a medical grade pressure sensitive adhesive coating provided on the lower face of the substrate layer.

When provided as such, the invented system has features which also make it advantageous for patients when compared with conventional systems, in that it offers the advantage of electrical stimulation for wound management and infection control, but does so in a miniaturized, wholly self contained reusable wireless adhesive patch-like device that can be worn on a patient's skin. To this end, the present invention overcomes the aforementioned and other disadvantages inherent in the prior art.

BRIEF DESCRIPTION OF THE DRAWINGS

With reference now to the drawings in detail, it is stressed that the particulars shown, are by way of example and for the purposes of illustrative discussion of embodiments of the present invention, and are presented for providing what is believed to be the most useful and readily understood description of the principles and conceptual aspects of the invention. In this regard, no attempt is made to show structural details in more detail than is necessary for a fundamental understanding of the invention, the description taken with the drawings making apparent to those skilled in the art how the several forms of the invention may be embodied in practice. Accordingly.

DETAILED DESCRIPTION OF THE PREFERRED EMBODIMENTS

Figure 1:
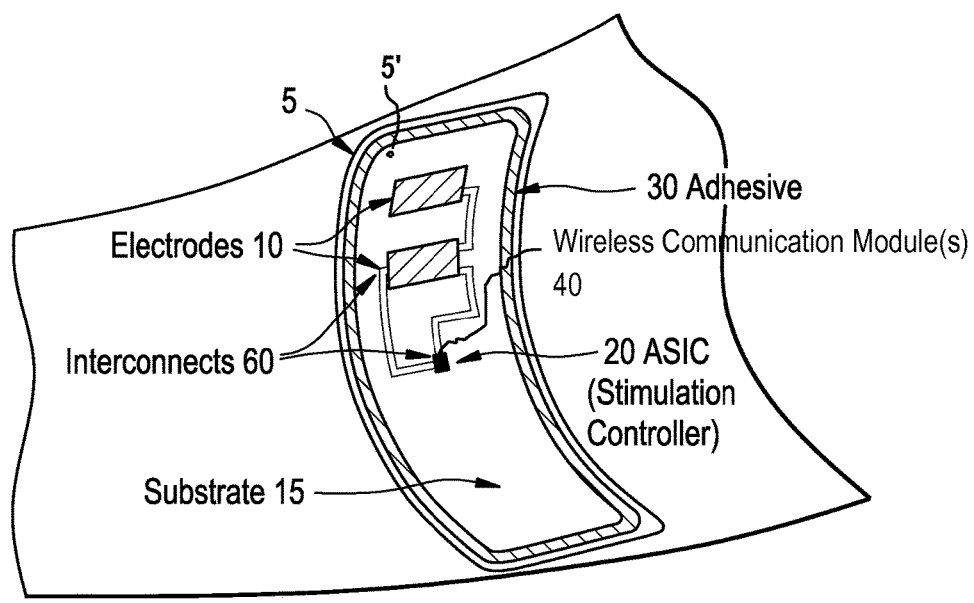
FIG. 1 is a photograph showing the physical appearance of an incomplete prototype of a wound treatment device as applied to a user, according to one embodiment of the invention.

Before explaining at least one embodiment of the invention in detail, it is to be understood that the invention is not limited in this application to the details of construction and the arrangement of the components set forth in the following description or illustrated in the drawings. The invention is applicable to other embodiments of being practiced or carried out in various ways. Also, it is to be understood that the phraseology and terminology employed herein is for the purpose of description and should not be regarded as limiting.

At its broadest level, the present invention relates to a medical device for treatment of wounds and/or infection(s) comprising at least one electrically powered patch comprising ISSD circuitry that includes interconnecting wires on a substrate layer; at least one stimulation controller, the stimulation controller being configured so as to provide variable stimulation patterns; at least one configuration of electrodes attached to the substrate layer and in electrical connectivity with the at least one stimulation controller; at least one bi-directional wireless communication link, the bi-directional wireless communication link or module comprising at least one RF or infrared based interface; at least one power source electrically coupled to at least one configuration of electrodes and at least one stimulation controller. The ISSD must also include means for encapsulating the circuitry; and an adhesive means for attaching the substrate layer to a treatment surface. The device is fabricated from thin and flexible materials to enable at least those surfaces that contact a patient skin to conform to the contour of the patient, and may be processed with thick or thin film deposition techniques and/or additive manufacturing techniques for application of the electrodes and other circuitry components, and may also provide for the power source to also feature a thin and flexible profile. By way of illustration, one recitation of exemplary additive manufacturing might include the following steps: 1) Load materials into appropriate low and high temperature cartridges; 2) Adjust temperature for each dispensing head to deliver appropriate material flows; 3) Define dispense rate and pressure based on materials characteristics; 4) Build up substrate in layers, with materials changes in each layer such that the conductive material is deposited in areas to form electrodes and vias defined by predetermined geometry and 5) Apply hydrogel over electrode surfaces on lower face of substrate.

The principles and operation of powered treatment devices according to the present invention may be better understood with reference to the figures. The figures show exemplary embodiments of the present invention and are not limiting.

Figure 2:
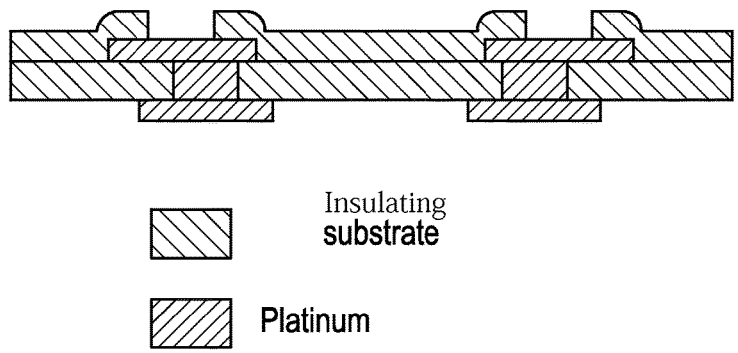
FIG. 2 is a schematic representation of an exemplary cross section of ISSD electrode-supporting substrate in accordance with one embodiment of the invention.
Figure 3:
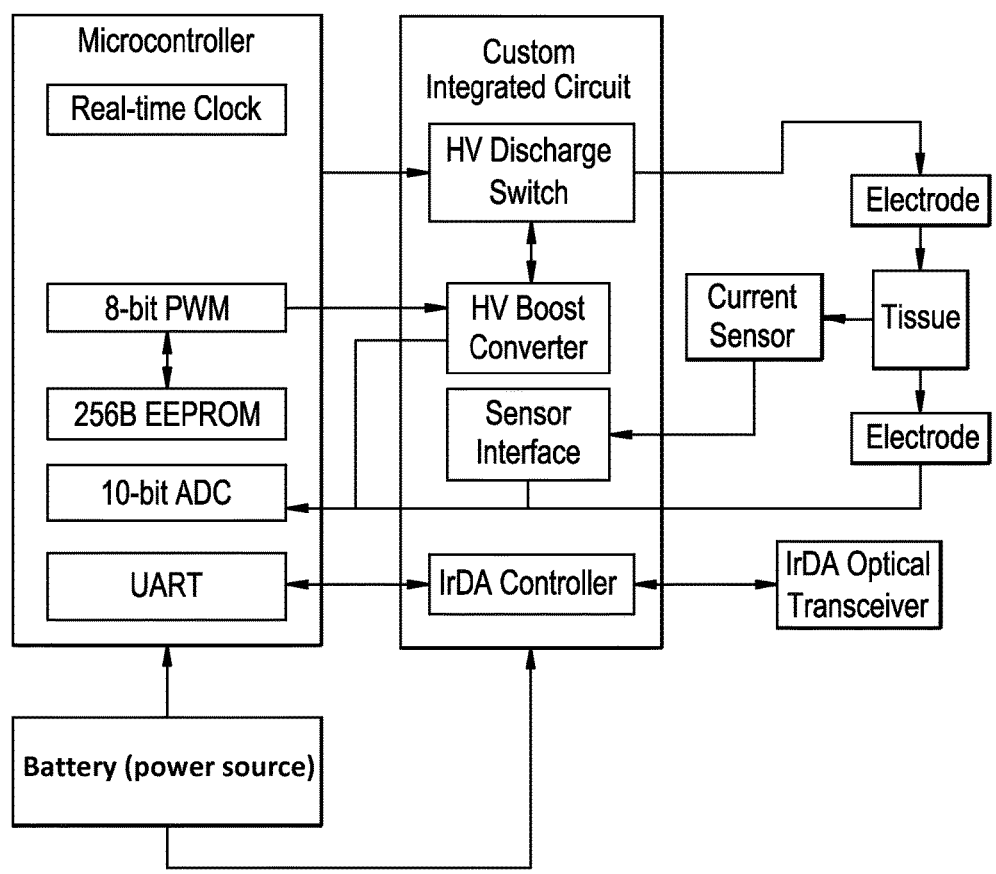
FIG. 3 is an illustrative block diagram of flexible ISSD circuitry 60 and related peripheral electronic components of the device according to one embodiment of the invention.
Figure 5:
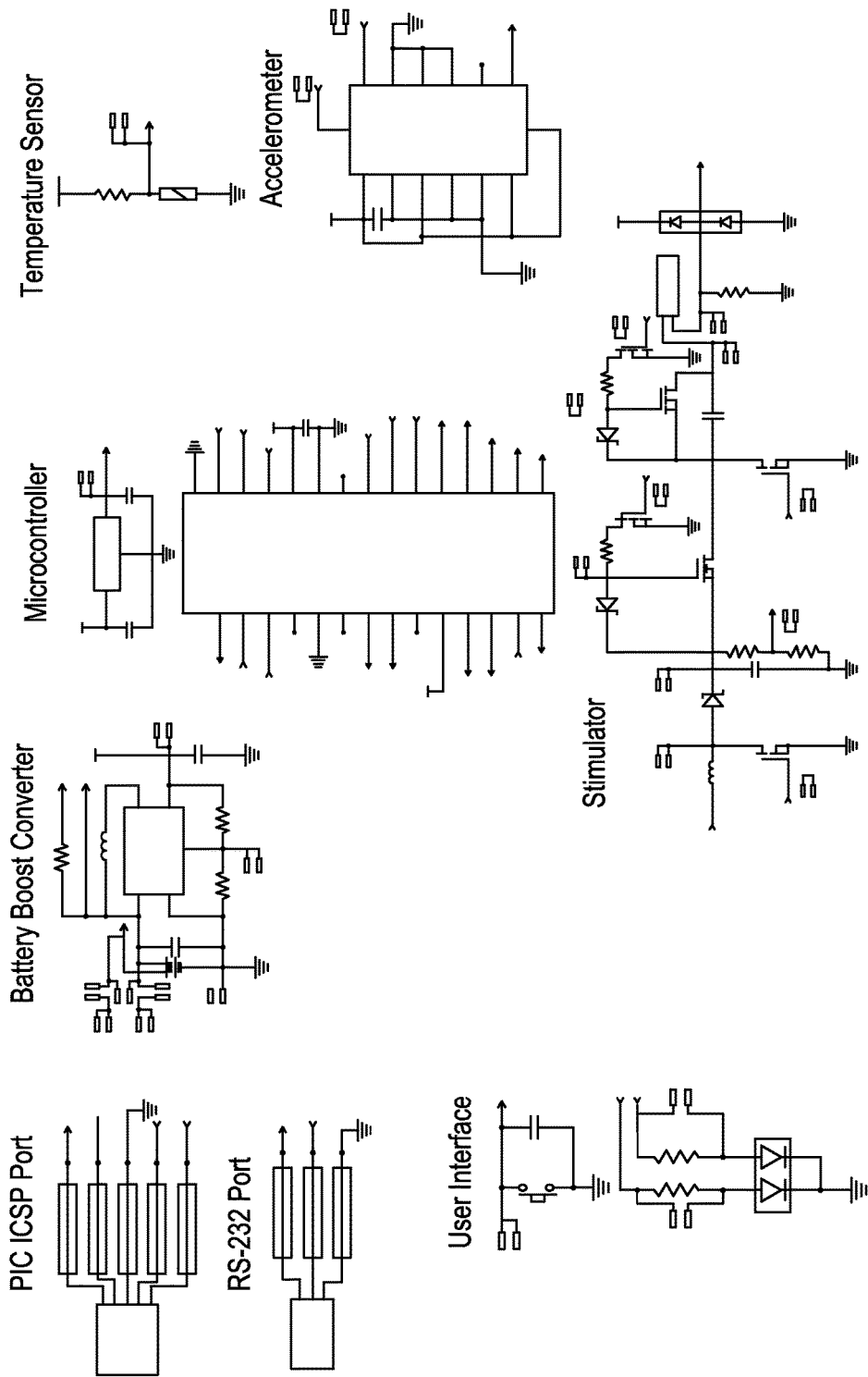
FIG. 5 is an electrical schematic diagram of one embodiment of the device according to the invention.

FIG. 1 shows one embodiment of a powered treatment device 5 as a patch 5', including only the stimulation electrodes and controller components of the ISSD circuitry 60, where the latter has been fully implemented as an ASIC in order to reduce size and improve flexibility of the device. FIG. 2 shows the schematic cross-section of the supporting substrate, which is optionally made of flexible materials. FIGS. 3 and 5 show two additional embodiments of stimulation controller 20, one (FIG. 3) which employs an ASIC (custom IC) to implement only the high-voltage, sensing, and wireless communication modules 40 of stimulation controller 20, and another (FIG. 5) in which off-the-shelf (OTS) components have been used to implement these functions. In both embodiments, stimulation controller 20 must be interconnected with the electrodes 10 through interconnecting wires 17 (not specifically depicted) and electrically connected with power source or supply 50, all of which are carried by a disposable substrate layer 15. Power supply 50 and stimulation controller 20 components can be electrically connected or alternatively, bonded to the upper face or side of substrate 15, or alternatively, power supply 50 and stimulation controller 20 components can be reversibly bonded, that is, they can be removed for reuse with a different substrate, by use of releasable connective elements. Thin metallic conductive electrodes and interconnects that are fabricated thereon. In certain illustrative embodiments, three different polymeric materials may be used to construct the flexible structures of the substrate layer 15, specifically materials such as polyimides, liquid crystal polymers, silicones, fabrics and thermoplastic polymers.

Flexible stimulating electrode 10 regions can therefore be microfabricated onto the lower face or side, which will be secondarily coated and/or printed with a medical grade pressure sensitive adhesive for attachment to the user. Because one key design concept underlying inventive device 5 is forward compatible upgradeability, it is provided with a flexible or adaptable architecture that allows for the potential for functional expansion such as multi-channel stimulation and biofeedback sensor capability, which is provided as an alternate embodiment of the present invention. The device comprises an integrated power supply and pre-programmable stimulation controller 20 system electrically and mechanically connected or otherwise mounted on the upper face of a flexible polymeric 'backbone' or substrate layer 15. The lower face of substrate layer 15 comprises areas of stimulating electrodes 10, applied using sputter coating techniques as described hereafter and as illustratively shown in FIG. 4. The device can be applied to the user with a medical grade pressure sensitive adhesive coating 30. In most cases, it may be helpful to have device 5 sterilized upon reuse or where not initially sterilized prior to placement over an open wound area of a patient. Many approaches may be used for this, and one illustrative sterilization could involve using an ethylene oxide, which is a low-temperature method that would allow device 5 to be fully sterilized, but would not damage the on-board electronics. In one embodiment, at least integrated power supply and pre-programmable stimulation controller 20 system of device 5 is capable of being sterilized, and to this end, may be fully encapsulated with a polymer coating or the like in order to enclose the same from moisture, and also, for protecting the electronic components therein during sterilization by chemicals, etc., after use.

Accordingly, the above may be summarized in accordance with one illustrative embodiment as a method for making electrode patterns in flexible substrates for use with an ISSD for wound therapy and infection control, as follows: (i) defining dimensions of a flexible substrate layer 15 using at least one STL (STereoLithography) file; (ii) defining topographical areas of electrically conductive materials (e.g., stimulating electrode 10 regions and electrically non-conductive materials using at least one STL; (iii) forming, through additive manufacturing techniques, the flexible substrate layer 15 having the aforementioned dimensions, formed from the group comprising polyimides, liquid crystal polymers, silicones, fabrics, and thermoplastic polymers; and (iv) forming areas of electrically conductive material materials (stimulating electrode 10 regions) and areas of electrically non-conductive materials based upon the defining of topographical areas of electrically conductive materials (stimulating electrode 10 regions) and electrically non-conductive materials, such that the forming areas of electrically conductive material (stimulating electrode 10 regions) and areas of electrically non-conductive materials is done through the aforementioned additive manufacturing techniques and is executed concurrently with the forming of said flexible substrate layer 15. The above is quite novel on various points, not the least of which concerns the advantageous provision of concurrent formation of flexible substrate layer 15 with electrically conductive material materials (stimulating electrode 10 regions) and areas of electrically non-conductive materials, a distinction which affords savings of time, materials and expense in processing, and which affords ease of production through portable additive manufacturing machines such as 3-D printers and the like. In regards to the use of STL file, the above method might further comprise imaging a patient wound, by various visual means such as surface scanners, photographic means, and/or visual and manual inspection, so as to ascertain various wound indicia, at least wound dimensions and shape. Once this resulting imaging has been created, the data points therefrom are converted or created by use of image processing software into at least one STL file. It is further noted that the customizing of flexible substrate layer 15 and the topographical layout or mask-like areas of electrically conductive materials (stimulating electrode 10 regions) and electrically non-conductive materials is done according to the imaging wherein flexible substrate layer 15 will have a certain shape and dimensions according to the shape and size of the wound and in consideration of the natural or inherent shape of the affected body part, while stimulating electrode 10 regions may have a certain layout or electrode density based upon the size and shape of the wound.

In a different embodiment however, the aforementioned overall method may alternatively be partially summarized as follows: (i) forming a flexible substrate layer 15 from the group comprising polyimides, liquid crystal polymers, silicones, fabrics, and thermoplastic polymers; (ii) using a pattern tool having an embossing surface with embossments to present a relief pattern complimentary to at least one desired relief pattern for a mask layer; (iii) forming apertures in the mask layer; (iv) forming a conductive material layer 10 on flexible substrate 15 based on the relief pattern of the mask layer; and (v) electrically connecting via the conductive material layer to output terminals of an ISSD the through apertures.

The controller circuitry or stimulation controller 20 provides functions such as timing, intermittent operation, and power monitoring, and combines with passive components, such as resistors, capacitors, an inductor and connective wiring (interconnecting wires 17, not specifically depicted), to produce stimulating waveforms that are transmitted to inventive flexible ISSD circuitry 60 which utilizes customized electrode 10 patterns therein to ultimately deliver ES to a patient wound. In generating the same, the duty factor of the high-voltage discharge pulses produced using stimulation controller 20 will be proportionally related to the average output power. The aforementioned passive elements are usually separate components, and may, in one embodiment, be mounted to a rigid circuit board (not depicted) and can be connected by printed wiring (also not depicted). However, a traditional rigid circuit board may not always meet design requirements (such as specific types of required flexibility) that may be required in some embodiments for stimulation controller 20. In either case, all electronic components herein must be minimized in quantity and size to maximize flexibility, as will be further discussed below.

Depending on the desired effect and system requirements, one may employ one of three possible illustrative embodiments, wherein the stimulation controller 20 comprises either: (i) two ICs (an IC microcontroller coupled with an ASIC stimulator); or (ii) a single IC (e.g., an IC microcontroller coupled with an OTS discrete stimulator); or (iii) a full-function IC, i.e. an ASIC that includes both stimulator and microcontroller functions, each of which is preferably miniaturized.

The ASIC embodiment may be either partially or completely based on an ASIC that may include all circuit functions required for actuation and sensing of the ISSD, as well as communication to the external computing device, such as a laptop computer, smart phone or the like, as contrasted with the discrete stimulator mentioned above which provides for these components separately. In either case, a high-voltage transistor may be required as part of a boost converter that provides the approximately 100-V level required for electrical stimulation in some circumstances. In one embodiment, all boost converter circuitry, excluding the aforementioned high-voltage inductor, diode, and storage capacitor components, could potentially be integrated onto the ASIC. Analog preamplifiers and analog-to-digital converter for sensing of electrode current and other biological signals of interest can also be fully integrated. Wireless communication circuits that comprise the wireless communications module 40 (discussed hereafter) can also be fully integrated, except for the infra-red (IR) photo diodes based embodiment required by the illustrative IrDA channel when used in a rigid circuit board-based embodiment. Because IR-based connectivity approaches require line-of-sight to a given partner device, in one illustrative embodiment, wireless communications can employ alternative wireless communication approaches such as the Bluetooth® Low Energy (version 4) standard, or other RF approaches for wireless communications module 40. The inventive flexible ISSD circuitry 60 may then comprise at least: (i) a stimulation controller 20 mounted on a circuit board which is in turn mounted on substrate layer 15, wherein the stimulation controller 20 has different embodiments, either two ICs (an IC microcontroller coupled with an ASIC stimulator); or a single IC (e.g., an IC microcontroller coupled with an OTS discrete stimulator); or a full-function ASIC that provides both microcontroller and stimulator functions, as discussed herein); (ii) a bi-directional wireless communications module 40 which includes connectivity to an IR interface (photodiode pair) or an RF interface required for wireless communication; (iii) a high-voltage boost converter circuit in electrical connectivity with stimulation controller 20, said high-voltage boost converter circuit comprising an appropriate high-voltage inductor/diode/storage capacitor as required by stimulation controller 20, said high-voltage boost converter circuit being charged to the aforementioned high-voltage level; (iv) power source 50 connected to the circuit board upon which stimulation board 20 is mounted; (v) stimulating electrodes 10 connected an interconnection means to the circuit board upon which stimulation board 20 is mounted; and (vi) the interconnecting means, wherein the interconnection means is provided for electrically connecting at least stimulating electrodes 10 with stimulation controller 20, the interconnection means illustratively including at least one or more components chosen from the group comprising: interconnecting wires 17 (not specifically depicted); thin film deposited structures; or thin film platinum interconnect structures in combination with a bonding, wherein the bonding is chosen from the group comprising wire bonding or flip chip bonding. In contrast to the full-function ASIC embodiment, the two-IC embodiment offers a separate high-voltage stimulator ASIC and microcontroller in order to permit straight-forward firmware upgrades and to minimize the cost of the ISSD, given that inexpensive OTS microcontrollers can be employed. This embodiment provides for the function of the stimulator to be preserved in the case where the microcontroller requires upgrading. The stimulator may be implemented using any preferred technology independent of the microcontroller and furthermore, may include sensory circuits such as for monitoring movement or other vital statistics in a user. In any case, the above ISSD circuitry can be encapsulated via an encapsulation means that protects the same from moisture and the like, all of which, when mounted on substrate layer 15, can be adhered to the skin of a user through the adhesive means described herein.

Regardless of the particular embodiment of stimulation controller 20, ISSD circuitry 60 may employ an aforementioned high-voltage boost converter circuit with a step-up loop that includes the aforementioned high-voltage transistor, and a storage capacitor that is rated for an illustrative maximum 100V, at an illustrative 100-nF capacity in order to maximize the voltage aspects of the overall system, and for increasing the (interchangeable) battery life of power source 50. In both the two-IC embodiment and the full-function ASIC embodiment, the step-up capacitor may be provisioned to be physically separate, off chip, but in electrical connectivity therewith. In the particular case of the two-IC embodiment, both ICs can be obtained in die form and can be 1) flip-chip bonded directly to metal traces on the flexible substrate, then sealed with protective coating, or 2) wire bonded to the lead frame of a standard surface-mount IC package that would then be hermetically sealed. The former is potentially smaller and more flexible, while the latter is simpler to manufacture and potentially more robust. Where an embodiment is desired that includes customized rather than OTS ICs, a custom IC (ASIC) could be fabricated using an illustrative 0.7-micron high-voltage CMOS foundry process provided by ON Semiconductor (available from ON Semiconductor of Phoenix, Ariz.), via the MOSIS service of Marina del Rey, Calif. Thereafter, it is noted that in the present invention, variable stimulation patterns are provided to accommodate different types of wounds and the changing treatment thereof over time. To this end, software can be pre-programmed on the microcontroller of a two-IC embodiment, or on the ASIC of a full-function ASIC embodiment. The various parameters that may be considered when providing such software within device 5 might, in one embodiment, be effected through usage of the below considerations set forth in Table 1, below.

TABLE 1

Specifications for conformable flexible integrated surface stimulation device (ISSD)

| Variable | Relevance | Criteria |
| --- | --- | --- |
| Safety | Prolonged contact with skin requires neither the materials employed nor the stimulation delivered will cause tissue damage | Substrate materials must be biocompatible & stimulation may be charge-balanced. |
| Reliability | In order to be effective, ES must be delivered as programmed. | Stimulation is ideally delivered consistently over an illustrative 7 day lifetime of the device. |
| Sterilization | Devices in contact with open wounds must be initially sterile to minimize infection. | May use illustrative ethylene oxide sterilization to achieve sterility while maintaining electrical functionality. |
| System configuration | | |
| Flexible | Chronic wounds occur on many parts of the body. | Conform to an arc equal in radius to a circumference of any rounded body parts. |

TABLE 1-continued

Specifications for conformable flexible integrated surface stimulation device (ISSD)

| Variable | Relevance | Criteria |
|---|---|---|
| Size | Device must be suitable for clinical use in a variety of wound locations. | Overall footprint will vary to fit target wound. |
| Electrode layout | Stimulating electrodes deliver therapeutic ES to the wound. | Electrodes to be located at the wound margins and can be patterned based on wound size and shape. |
| Low-profile & lightweight | Not interfere with overlying bedclothes or cause high pressure if accidentally lain on. | Maximum height less than 3 mm in one illustrative embodiment. Maximum weight less than 15 g in one illustrative embodiment. |
| System function | | |
| Wound occlusion | A moist microenvironment provides optimal wound healing | Maintenance of adherence to skin for up to 7 days with full wound occlusion. |
| User-friendly interface | Clinical acceptance requires ease-of-use. | Includes a customizable design for an intuitive GUI for selection and control of stimulation patterns. |
| Programmable | Optimal stimulation variables for ES therapy can be defined. Stimulation profiles can be applied intermittently or continuous, for duty cycles from 5 min/day to 24 h/day. | Stimulation pulse variables making up the respective profile(s) may be based on data from prior clinical studies, illustratively described as:<br>　　　　　　Range　　　Increment<br>Pulse width　0-200 µs　　5 µs<br>Amplitude　　0-20 mA　　0.5 mA<br>Frequency　　0-20 Hz　　1 Hz |
| Power supply | Independent power supply, capable of 7 days use is required for un-tethered system. | Battery-powered, capable of up to 7 days continuous use. Battery will last longer with intermittent use. |

As mentioned above, the central core of present device 5 is comprised of a flexible polymeric biomaterial insulating substrate (substrate layer 15) on which the flexible power supply 50 and rigid stimulation controller 20 will be attached along with the thin metallic electrodes and interconnects that are fabricated thereon. In certain illustrative embodiments, three different polymeric materials may be used to construct the flexible structures of the substrate layer 15, specifically materials such as polyimides, liquid crystal polymers, and thermoplastic polymers. In one particular embodiment, a combination of thick polyimide foils and thin film resins may be used for producing substrate layer 15 in order to meet the requirements for the device to be durable for longer periods in different environments, such as those encountered where use is needed for say, one week of continuous use in moist environments. One illustrative example of production of this variant of substrate layer 15 within the overall context of the present invention may be seen in FIG. 4, which details an exemplary process sequence for fabricating a flexible polyimide ISSD substrate. Substrate layer 15 may optionally be manufactured from any polymer material that is suitable for flexible electronics and biomedical uses according to a process that utilizes patterning that creates via structures thereon between the aforementioned circuit components through use of a micromachining step, or any suitable material which can accommodate the powered treatment device components. Suitable materials include, but are not limited to woven material, non-woven material, polymers, or a combination thereof, and, in the case of woven materials might alternatively include the usage of smart fabrics which employ conductive traces on or within the fabric whether purely woven, knitted, sewn, couched, or whether provided as e-broidery and/or printed structures. Nevertheless, in one illustrative embodiment, substrate layer 15 may alternatively be made from liquid crystal polymers, polyimides, vinyl materials or polyester. Optionally, substrate layer 15 can be made up of a plurality of materials, which can be stacked or connected in a co-planar way by any suitable attachment means. In some embodiments, base layer substrate 15 is made up of one continuous piece of material. Substrate layer 15 may readily facilitate attachment of the overall device 5 to a desired body area. Attachment mechanisms may include but are not limited to medical grade adhesives, adhesive strips, suction cups and/or any combinations thereof. It has also been found that lower cost medical grade pressure sensitive adhesives such as Dermabond® (2-octyl cyanoacrylate, marketed under the aforementioned trademark by Johnson & Johnson of New Brunswick, N.J.) can be used, in one embodiment, to attach substrate layer 15 to intact skin. On removal, this type of medical grade pressure sensitive adhesive preferentially adheres to the substrate material, thus causing no skin damage, and can remain strongly adherent after many hours or days.

Figure 4:
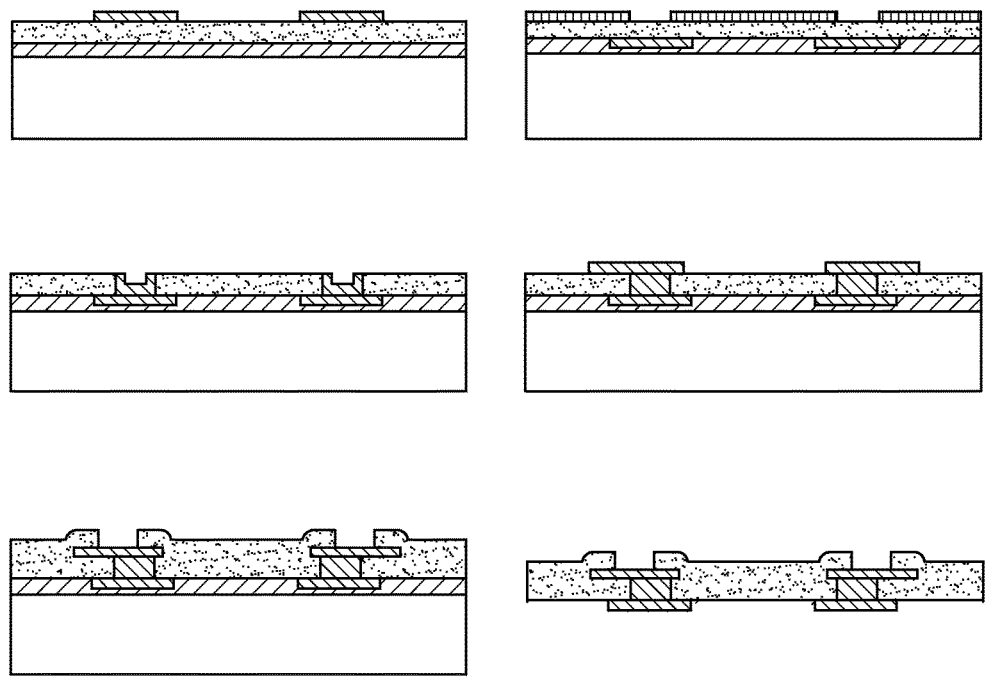
FIG. 4 is schematic cross-sectional views illustrating an exemplary fabrication sequence, reading in order from left to right, with polyimide substrate used in the device in accordance with one embodiment of the invention.

In one embodiment, the present invention provides flexible ISSD circuitry 60 to be situated on substrate layer 15 that is processed from LCP for component side isolation, or as depicted in FIG. 4, is alternatively processed from an illustrative spin-castable polyimide material that utilizes patterning processes in order to create via structures between the circuit components of flexible ISSD circuitry 60. One exemplary approach utilizes a micromachining step, such as a KOH-based wet chemical etching step, in order to create the via structures depicted in FIGS. 2 and 4. Such an etchant is effective in removing polyimide, and the use of etchant-resistant materials such as platinum for electrodes 10 and illustratively, chromium for the metallic etch mask can offer good resistance to the etchant. Alternatively, plasma etching, laser micromachining or other material removal techniques can be utilized to realize the same structures, but in either case, successful fabrication of the flexible ISSD circuitry 60 is critically dependent on the fabrication of effective interconnect structures that fill the microfabricated vias. Simultaneous electroplating on both the sidewalls and the bottom surface of the vias enables complete filling within an illustrative current thickness range of say, 10 microns. Alternative electroplating options may be afforded under ultrasonic conditions or with the use of 'filler' materials. Following fabrication of substrate layer 15 and interconnects thereon, the discrete components thereof can be mounted at designated locations on the (illustrative polyimide) substrate layer 15 using a conventional electronics packaging adhesive. Electrical connections that may comprise a part of an interconnection means or in one embodiment, interconnecting wires 17, between the discrete components and the thin film platinum interconnect structures may, in one illustrative embodiment, be made by wire bonding. Flip chip bonding can also be used to make secure electrical connections. The electrical connections can be mechanically secured, electrically isolated and environmentally protected by a third polyimide film of roughly the same thickness as the discrete components (0.5 mm) so as to ensure complete coverage of the wire bonds. It can be locally applied so as to not interfere with the global flexibility of the substrate. After localized polyimide encapsulation, the polyimide substrates can be removed from their silicon wafer pairs by a mild acetone soak or other appropriate methodology as known in the art.

In an additional embodiment (not specifically depicted), the present invention provides a method of production of device 5 and details of which, in terms of the illustrative materials and fabrication, are discussed henceforth. The central core of the device 5 is a flexible electrode-supporting substrate 15 comprised of a Liquid Crystalline Polymer circuit material (LCP) sheet with an 18 μm copper cladding layer on one of its surfaces, not necessarily depicted in FIG. 4, but which is nevertheless roughly similar to the fabrication sequences of which are illustratively described in one embodiment as seen in FIG. 4. In one embodiment, the structures of electrodes 10 are fabricated on the non-copper clad user-applied side of the insulating substrate 15 by photolithographic patterning, platinum thin film sputtering, and lift-off patterning. Electrodes 10 can be made of any suitable material, such as zinc, copper, manganese dioxide, iron, magnesium, silicon, sodium, silver, silver/silver chloride, carbon, graphite, platinum, nickel, gold, lithium or a combination thereof. Optionally, electrodes 10 can be made by any suitable technique. In some embodiments, electrode is made by a suitable printing technique. Electrodes 12 can be disposed in any suitable way on substrate 15 in spaced relation to power source 50 and electrically connected to power source 50 in any suitable way, or as described herein. Vias for vertical electrical interconnects between the two sides are then formed through the LCP by laser micromachining or plasma etching from the copper-clad component side to the back of the platinum electrodes. Platinum is sputter deposited on the sidewalls of the vias prior to electroplating to form a vertical interconnect between the bio side electrodes and the stimulation circuitry on the component side, as depicted in FIG. 2 and FIG. 4. Lateral interconnect structures are then fabricated by lithographic patterning and copper etching. The upper surface of the substrate 15 can be composed of a flexible or partially flexible barrier material (optionally part of the aforementioned encapsulation means) that provides a safe interface with the patient's environment, yet protects the electrical components from direct exposure to moisture, especially for the sensitive and delicate microprocessor chips and electrical interconnects. This packaging or encapsulation means must not impede the flexibility of the substrate, be impervious to impurity diffusion, be mechanically durable and be electrically insulating. Parylene® is one embodiment for this application since it meets the design requirements and has been found to be a suitable candidate coating material for implanted medical devices. The lower side of substrate 15, which is intended to be applied to the skin of a patient, is secondarily coated with a medical grade pressure sensitive adhesive for attachment to the user, as part of the aforementioned adhesive means. The metalized surfaces on the component side are passivated by the application of a vapor deposited Parylene® film and/or spin-castable polymer. Windows into the passivation layer can be formed by laser micromachining or plasma etching to facilitate electrical connection with discrete components, and can provide patterning in varying layouts as may be required for customized electrode patterns in specific applications involving particular (size/type) wound remediation and the like. In order to meet the need for customization, the above offers an aspect of provision for modularity wherein the electronic components of ISSD circuitry 60 can be mounted on a second LCP sheet that serves as the substrate for the reusable electronic components. Interconnect structures are fabricated on this LCP sheet using the methods described above. Therewith, further connections between the electronic components and the interconnect structures, including the interconnection means, can also be made by wire bonding or flip chip bonding. The reusable component substrate can then mounted on the electrode-supporting substrate using a conventional packaging adhesive. The reusable component substrate is mechanically secured, electrically isolated and environmentally protected by an encapsulating means of polymer film of roughly the same thickness as the discrete components (0.5 mm) so as to ensure complete coverage of wire bonds. The upper surface of substrate 15 of device 5 is thus composed of a flexible barrier material that provides a safe interface with the patient's environment in such a way that protects the electrical components but does not impede flexibility. Medical grade silicone can also be used to encapsulate the electronic components in order to further ensure biocompatibility, electrical compatibility as an encapsulating material for microelectronics, and for ease of overall application.

In terms of power supply, device 5 provides for varying approaches to power source 50, which typically requires provision of a requisite voltage that is necessary to generate stimulating waveforms. Power source 50 may comprise single-use batteries, however discharge characteristics must be repeatable to ensure reliable delivery of pre-programmed stimulation patterns. A flat power discharge profile that will provide consistent power for longer periods (e.g., approximately 7 days or so) of stimulation is desirable, although the inventive electronics design also allows for a somewhat sloped discharge profile. Therefore, any battery chemistry can be used. The battery must be thin, small, durable and strong. Power supply or source 50 can be modified in 1.5-V increments as necessary, but generally will be either 1.5 V or 3.0 V. To this end, power source 50 is ideally thin and flexible as specifically described below in one illustrative embodiment, but it can nevertheless be of any suitable size and shape that can accommodate the aforementioned requirements. In one embodiment, the power source 50 is depicted as a single electrochemical cell. However, power source 50 need not be limited to one cell, but may include a plurality of connected electrochemical cells, galvanic cells, batteries, with/without electronics configured to regulate the electrical potential (voltage) to the level required by the particular body area of the subject. In some embodiments, the current and or voltage supplied by the power source is fixed and cannot be adjusted by a user, although stimulation controller 20 can provide for any direct stimulation capability. The thickness of the illustrative electrochemical cell or power supply 50 may be in the range of about 4-20 mm thick. By way of example, a suitable electrochemical cell may be a button or watch battery, such as a lithium coin battery providing approximately 40 mA-hr at 3V, may be utilized. However, this may in some cases prove too heavy and bulky, and as such in alternative embodiments, power supply 50 may be provided in a 1.5-V cell with step-up circuitry, with total battery current consumption for a nominal stimulation pattern of ~1 mA, thereby giving a battery life of say, 240 hours with a 15% stimulation duty cycle, or may also be provided as a thin cell applied using a suitable printing technique. Recent developments in battery technology have led to the development of very low profile, flexible 'ribbon' batteries, such as PowerPaper™ batteries (available from Graphic Solutions, Chicago, Ill.), which are ultra-thin (<1 mm thick) flexible batteries that can be directly printed onto a variety of surfaces. The cathode and anode layers of these illustrative batteries are fabricated from proprietary ink-like materials, thereby creating a 1.5-V battery that is thin and flexible and does not require bulky casing or encapsulation. In addition, the materials used in this illustrative battery, zinc and manganese dioxide, are classified by the Federal Drug Administration (FDA) as environmentally friendly, non-hazardous and may be disposed of without restriction. These types of batteries are capable of providing up to 1 mA continuous current. However, these ribbon type batteries often do not provide adequate power for longer periods, and may be useful for more temporary applications Terminals for connection thereto may be located in any desired location to connect to the specific cell employed and may acquire any suitable shape and size, depending on the specific application.

In one alternative embodiment, stimulation controller 20 may include a reusable stimulator PCB (35×20 mm) capable of producing pulses up 21 mA in amplitude and 250 μs in duration, powered from a single 450 mAhr rechargeable Lithium Polymer battery such as the PowerStream GM043436-PCB to power the device. The benefit of such a exemplary battery is that it provides sufficient power to deliver reliable stimulation to a large wound for an extended period of time (for example, up to seven days) and can be recharged for use with a different substrate on the same patient. As can be appreciated, this represents a significant advance in terms of overall performance.

Figure 6:
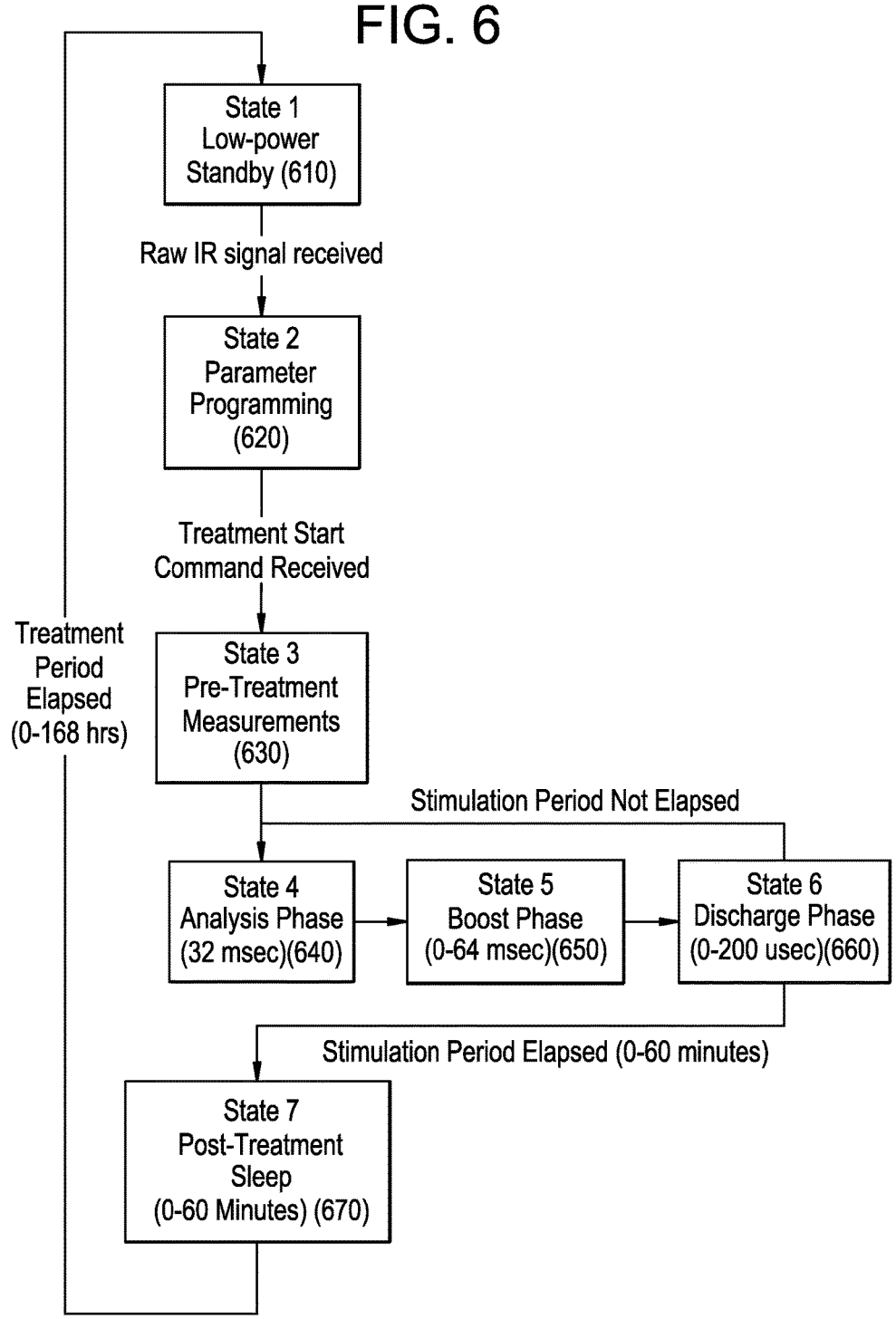
FIG. 6 is an operational flow diagram illustrating an exemplary treatment protocol utilized with one embodiment of the invention.

The invented device may be provisioned as a single-channel, single-pattern stimulator device, which would require a system control switch (not specifically depicted) to switch the operating state of device 5 between one of two states, off and on. However alternative embodiments of the device will also include the potential for multiple stimulation patterns and feedback to the clinician or technician through stimulation controller 20, which as discussed above, offers the capability for more sophisticated control, interrogation and feedback options. In providing such features, bi-directional wireless communication module 40 may further include an RF or an infrared communication link and protocol (such as an IrDA-based infrared communication link and protocol) that allows the ISSD to communicate via multiple channels with outside partner devices (not depicted) such as computers, smart phones, tablets, lap tops, etc., so as to allow system control and retrieval of sensor data without a physical connection to device 5. In such an illustrative embodiment, the selected communication protocol might allow up to 256 units to be used in the same vicinity. If based on illustrative IrDA-type optical components, it is noted that the inherently narrow transmission focus thereof (approximately a 30 degree cone) can mitigate potential communications issues emanating from inventive device 5, because selection of a given partner device requires pointing the partner device at the inventive device 5 being programmed at any given time. Communication software can further be utilized for modifying stimulation parameters in stimulation controller 20 and for displaying stimulation waveform graphs on the partner device. To this end software to allow system control and retrieval of sensor data (e.g., outside control adjustment and feedback upload) using the link might be provided in accordance with the illustrative steps 610-670 as outlined in FIG. 6. Sensor data and other status parameters can be uploaded to the partner device and displayed to facilitate any necessary adjustments. Afterwards, any (bio) data provided from the sensors (electrodes 10) can be uploaded to the partner device for further analysis offline, if desired by a given medical professional. To this end, the aforementioned optional software package may also be provided with a graphical user interface (GUI) for use on a partner device connected to the inventive device, as employed by a medical professional.

When provided in accordance with the above, treatment device 5, including all device components, has an overall thin and flexible profile, which may suit the contour of a body area of a subject. Treatment device 5 may therefore be of any size, color and shape suitable for application to a desired body area. In some embodiments, the thickness of device 5 may limited to 10 mm to ensure flexibility, but may be thicker in other applications. The thickness of device 5 may also be dependent upon the type of material used and the flexibility of that material. In some embodiments device 5 may be partially and/or completely disposable. To this end, in some embodiments substrate layer 15 may be disposable, while the ISSD circuitry 60 may be reusable (modular, and therefore easily switched to anew replacement substrate layer 15), or alternatively, the whole device 5 may be deemed disposable. Regardless of which embodiment is chosen, device 5 must be stable over a wide range of temperatures and humidity levels, and may be used over all body areas of a patient or user, and to this end, may be designed or customized to fit any area of the body and to have any desirable size, according to the area to be treated. By way of further note, electrodes 10 can also be customized in terms of overall number, size, and distribution on substrate layer 15. The customization of electrodes is often less important when the application usage of device 5 is for pain treatments (which are better customized through the use of amplitude variations and the like for varied pain states). In the ease of wound and/or infection treatment, however, it is often important to be able to vary the aforementioned design parameters in order to adequately treat different types and sizes of wounds or states of infection, as well as underlying presenting basis (e.g., whether planktonic or biofilm in nature).

The device of the present invention can therefore be a fully integrated device or can be part of a kit with removable components so that the covering, battery source, etc. may be replaced as needed. The device may also be removed from the body area at the end of treatment time. Time of treatment can vary, and accordingly, the device in some embodiments can be removed from contact with the body area after a time period which can be predetermined, upon expiration of a timer, or which can be determined according to the desired treatment and/or until no more improvement can be seen. The treatment can optionally be a one-time treatment, or can be repeated in suitable time intervals any suitable number of times. Use of the present invention can facilitate temporary alleviation and elimination of the above conditions. Duration of effect can therefore be affected by time and frequency of application, stimulation pattern variables, type and amount of current used, and severity of condition. In one embodiment, the device is a dermal patch configured for home use. In other embodiments, the device can be applied in a supervised environment. To this point, treatment according to the present inventions may be beneficial in all body areas. Being thin, flexible and versatile in shape and form, the devices of the present invention can be designed to fit any area of the body and to have any desirable size, according to the area having the disorder.

Novel Electrotherapy for Acute Infected Wounds as a Method for Inhibiting Planktonic and Bacterial Activity.

It is understood that wound infection delays healing and increases mortality. Increasingly, antibiotics are showing reduced efficacy in the face of multi-resistant bacteria. The increasing prevalence of multi-resistant bacteria indicates that novel approaches to infection control are needed as both alternative and adjunctive therapies to standard antibiotic regimes. Such infections are particularly challenging when biofilms are involved given that biofilms have protective coatings made up of polysaccharides and other components that shield the given bacteria colony in the biofilm from treatment. Hence, there is a clinical need for an intervention that can reduce incident infection, clear existing infection and accelerate healing, especially when a patient has an infection that exhibit biofilm colonies. The novel use of Electrical Stimulation (ES) as disclosed herein has the potential to address this clinical challenge by reducing incident infection, clearing existing infection and accelerating healing.

Both planktonic and biofilm bacterial wound infections can be positively impacted by the novel use of ES to improve healing rates in both acute and chronic wounds can be effectively treated. The novel system and methods relating to ES treatment as disclosed herein increases local metabolic activity of cells and tissue oxygenation (flesh healing), disrupts existing biofilm colonies, and even inhibits biofilm formation from the outset. Additionally, the novel system and methods relating to ES also reduces acute wound infection by bactericidal effects on many strains relevant for complications of acute traumatic wounds. These effects may be due to electrolysis products or to increases in bacterial membrane permeability. Sustained ES application in accordance with the present invention is bactericidal when applied to infected but unwounded skin, and additionally, increases blood flow and capillary density in compromised wounds, thereby speeding up healing rates thereof. The resulting efficacy of the present invention appears to vary with stimulation profile, which in at least one illustrative case, is that the primary ES factor being current density, thereby implying that the bactericidal effect is electrochemically mediated. Low-intensity electric fields (e.g., those having a field strength of 1.5 to 20 V/cm and current densities of 15 $pA/cm^2$ to 2.1 $mA/cm^2$) can combat the inherent resistance of biofilm bacteria to biocides and antibiotics. Biofilm infections are a well known for being difficult to eradicate, especially when compared with planktonic cell of the same species of bacteria. The novel application of electrochemically mediated treatment with the inventive device offers a bioelectric effect that reduces the concentrations of the antibacterial agents needed to kill biofilm bacteria when compared with those needed to kill planktonic cells of the same species. The electric field from the novel ES device and method can aid the disruption or penetration of the antibacterial agents through the protective polysaccharide and other coatings that shield the biofilm. This penetration is, in one illustration, accomplished by a form of electrophoresis that may augment the electrochemical generation of resulting surface agents that enhance the efficacy of given antibacterial.

In accomplishing the above, the present invention therefore provides for a method for using an ISSD for wound therapy as well as for infection control, including for difficult infections like biofilm based infections. To this end, in one illustrative embodiment, the method might comprising the following steps of: (i) assessing a wound and/or infection state; (ii) applying a customized ISSD patch with electrodes 10 and a flexible substrate 15 immediate to a wound location; (iii) attaching an encapsulated power/control module 20 to said customized ISSD patch with electrodes and the flexible substrate 15; (iv) setting ISSD controls, including setting at least one of the following of a power profile or at least one customized stimulation pattern; (v) initiating ES power and sequences on a resulting set up; and (vi) monitoring wound and at least one of the following of battery power, impedance, and temperature. Additionally, the inventive method may further comprise: (vii) formulating a customized electrode 10 pattern according to the step of assessing a wound type and infection state; (viii) fabricating said customized electrode 10 pattern by various techniques, including foil, additive or 3-D printing techniques, or alternatively, by traditional deposition techniques; and (ix) combining said customized electrode 10 pattern with selected flexible substrate 15 as a resulting patch 5' for patient wound therapy. Also the method may additionally include: (x) attaching an encapsulated power/control module 20 to customized ISSD patch 5' with electrodes 10 and a flexible substrate 15, and additionally; (xi) combining a customized disposable flexible substrate 15 with a re-usable, sterilizable encapsulated power/control module 20. What is specifically meant by encapsulated power module 20 being sterilizable or having a sterilizable encapsulation is that it is encapsulated in a plastic or other type of complete encapsulation that can seal off the electronics therein from the harmful effects of water or chemicals that may be used in the course of sterilization at a level that can kill microorganisms. Separately, it is noted that optional provision is contemplated for attaching a power source 50 comprising a rechargeable battery (power supply 50) with capacity of at least 450 mA-h.

In applying the above inventive method in a clinical setting, one illustrative approach calls for the novel approach of providing treatment and monitoring of wounds and infections concurrently or at same time. Thus, one employing this novel approach might be able to simultaneously or concurrently treat and monitor wounds and infections through the following steps of: (i) applying a customized ISSD patch 5' with electrodes 10 and a flexible substrate 15 immediate to a wound of a patient; (ii) electrically connecting an encapsulated power and control module 20 to customized ISSD patch 5'; (iii) establishing a wireless communication connection for remote control between a control module 40 and encapsulated power and control module 20; (iv) monitoring ongoing wound and infection indicia over a course of time; (v) establishing, based upon the preceding step of monitoring ongoing wound and infection indicia over a course of time, a dynamic (e.g., potentially revisable depending on changes to identified wound and infection indicia) wound treatment ES profile for execution over said course of time; (vi) establishing, monitoring ongoing wound and infection indicia over a course of time, a dynamic infection control ES profile for execution over the course of time; and (vii) executing, over the course of time, said dynamic wound treatment ES profile and the dynamic infection control ES profile at the control module. Additionally, the method may further include processing steps (iv)-(vi) through an open loop program option or a closed loop option. An open loop program option may be further described in one embodiment as: In the open-loop embodiment the medical professional will receive a report of the wound/infection status transmitted from the ISSD. The medical professional will be able to alter the ES profile remotely to maintain optimal treatment. In the closed-loop embodiment, the medical professional will receive a report of the wound/infection status transmitted from the ISSD and the ISSD will adjust the ES profile in real time based on the wound indicia being monitored.

In the above, it is noted that the wound and infection indicia may include particulars such as wound temperature, wound impedance, and wound pH. Monitoring such particulars is advantageous inasmuch as it has now been found that impedance decreases over time where a wound is healing and/or where infection presence is decreasing, and similarly, temperature exhibits similar paradigms of decrease. Additionally, the step of monitoring while treating is further advantageous in that all wound healing (and infection resolution) goes through different stages over time, and consequently, it has now been found that the inventive approach of utilizing treatment factors such as pulse width, pulse interval, and interpulse amplitude variables is to be pursued in a dynamic fashion, whereby the same are increased or decreased over time increments and over the overall course of time in response to the respective stage of healing or infection resolution. Similarly, the monitored presence of say, just an infection without wound presence normally entails utilization of different treatment factors, such as a relatively lower current than that which is normally employed compared to wound healing. Also similarly, monitoring for biofilms as opposed to planktonic infections may alter the treatment factors, just as monitoring for an acute infection turning into a chronic infection, because a chronic infection (unlike acute) may normally imply wound treatment factors in addition to purely infection treatment factors. Hence, the infection state as monitored can drive the electrical pattern and any accompanying customization therewith.

It is further noted that the aforementioned method for simultaneous treatment and monitoring of wounds and infections may provide that the step of monitoring ongoing wound and infection indicia over a course of time, as well as the step of executing the dynamic wound treatment ES profile and the dynamic infection control ES profile may both be effectuated remotely through use of wireless communication, such as bi-directional wireless module(s) 40 as depicted in FIG. 1. In some cases, control module 20 has wireless communication module 40 encapsulated therewith.

Illustratively, the following particulars were observed in one exemplary usage of the inventive system and apparatus for treating wound infections:

Example 1—Electrical Stimulation (ES) Promotes the Healing of Ischemic Wounds

Approach:

The effects of varying clinically relevant ES variables were evaluated using a modified version of the Gould F344 rat ischemic wound model. Stimulation was delivered using the novel lightweight integrated, single-channel, current-controlled ISSD as further disclosed herein. Customized ES patterns in accordance with the novel approach disclosed herein were utilized, which, in this illustration, included stepwise variation, indicating the effects of five (5) different stimulation paradigms within an appropriate current density range to be studied. These five (5) different illustrative stimulation paradigms included: Pattern 1: pulse amplitude 4 mA, pulse width 100 μs, interpulse interval 50 ms; Pattern 2: pulse amplitude 2 mA, pulse width 100 μs, interpulse interval 50 ms; Pattern 3: pulse amplitude 6 mA, pulse width 100 μs, interpulse interval 50 ms; Pattern 4: pulse amplitude 4 mA, pulse width 150 μs, interpulse interval 50 ms; and Pattern 5: pulse amplitude 4 mA, pulse width 100 μs, interpulse interval 40 ms. Within each of the aforementioned five (5) respective groups, 8-10 animals were treated for 28 days or until the ischemic wounds were healed, and additionally, 5 animals were treated for just 12 days. Eight (8) rats received sham devices as a control. A quantitative multivariable outcomes assessment procedure was used to evaluate the effects of ES.

Results:

Ischemic wounds treated with a decreased interpulse interval (IPI) had the highest rate of complete wound closure at three (3) weeks. Wounds treated with decreased pulse amplitude (PA) had a lower proportion of closed wounds than sham (control) ischemic wounds and showed sustained inflammation with a lack of wound contraction.

Results According to Specific Illustrations of Exemplary Stimulation Variable Settings:

Acute Infected Wounds:

ES was delivered by the ISSD with a 10% duty cycle for up to 28 days or until all treatment wounds appeared to be fully healed. The median values selected for proof-of-concept testing were pulse amplitude 11 mA, pulse width 110 μs, pulse frequency 17 Hz. By 21 days post-injury, ES treated infected wounds were 84% smaller than untreated control wounds.

Chronic Wounds:

Optimal stimulator parameters will vary depending on wound type and extent, but benefits have been seen for a wide range of parameters. The optimal treatment parameters for delivery of effective ES for chronic wound therapy are therefore guided by the underlying physiological effects. In pre-clinical testing, ES delivered by the ISSD with a 10% duty cycle with pulse amplitude 4 mA, pulse width 100 μs, interpulse interval 40 ms had the highest rate of complete wound closure at 3 weeks.

Conclusion:

The systematic study of innovatively varying ES paradigms using the novel ISSD provides insight into the advantageous use of ES in ischemic wound healing. This conclusion is based upon the following findings. Specifically, clinically appropriate ES can more than double the proportion of ischemic wounds closed by three (3) weeks in this model. Ninety percent (90%) of wounds treated with a decreased IPI healed by twenty-one (21) days compared with only twenty-nine percent (29%) of ischemic wounds treated with decreased PA, which appears to inhibit healing.

It is further noted that, in the above example (as well as for other illustrations of the novel method) the innovative ISSD undergirded much of the advantageous results. Specifically, the innovative delivery of power has superior reliability, and is able to deliver ES over an extended period of time that heretofore has not been realized. Thus, the innovations of: customized electrodes, customized pulse, customized width, intermittent v. continuous pulsing, etc as disclosed herein are indeed novel, and furthermore, the actual use of ES in both acute and chronic wounds (especially in combating troublesome biofilms) is heretofore unknown.

The above approach can be employed in human (in vivo) applications in order to speed up healing of both chronic and acute wounds, as well as for reducing infections of both planktonic and biofilm types, especially in topical rather than systemic applications. In doing so, one illustrative method might include some or all of the following exemplary steps: 1) Assess wound type and/or infection type; 2) Formulate customized electrode pattern by considering, for example wound size; 3) Fabricate customized electrode pattern by various techniques, including additive or 3-D printing techniques, or alternatively, by traditional deposition techniques, combine with selected flexible substrate as resulting patch for patient wound; 4) Apply patch immediate to wound location, attach ISSD controls; 5) Set power profile or customized profile in accordance with particulars described elsewhere herein; 6) Initiate ES power and sequences on resulting set up; 7) Monitor battery power, impedance, and temperature. Thereafter, if the measure impedance increases over time from a base impedance as measured, then that means that the target wound is healing. Also, operators should monitor the measured temperature at the wound site, as this factor is typically related to infection level, such that elevated temperature indicates infection activity overall, although it is to be noted that this normally is more indicative of planktonic infections which are often more biologically active, rather than biofilm based infections which tend to be more stable; 8) Retain patch with ES treatment on for a specified period of time. In one exemplary usage where the system is complimentary to antibiotic use, one illustrative period of use is for approximately seven (7) days. Note that this treatment period may vary, in accordance with wound type, patient history, electrode customization and ES pattern profiles and current density chosen by the medical provider.

Of additional note, is the understanding that in some embodiments, one may dispense with steps 2 and 3 in cases where the customized electrode pattern has already been fabricated off site and combined with the flexible substrate for use as part of a readily accessible stockpile or pre-configured customized patches that are suitable for a specific wound types. Such provision would eliminate the need to have fabrication equipment on site. In such cases, the stock customized patches could be respectively produced in mass according to shape and size (depending on the areas of body being treated) and for type of wound (e.g., a more electrodes or a higher density of electrodes in a given electrode pattern might be used for wounds such as chronic wounds, or for acute traumatic or surgical wounds, and the like).

It is noted that the aforementioned can be applied to more than just the actual flesh of human patients undergoing the innovative ES treatment with the novel apparatus. Specifically, the novel method and apparatus can also be adapted in an alternate embodiment, to medical device surface treatments, such as for oral biofilms, mouth guards, orthodontics, tracheostomy tubes, endotracheal tubes, indwelling catheters as well as other classes of catheter, and in general other medical devices that are susceptible to infections, especially those caused by biofilm buildup. In adapting to the same, an exemplary approach might be as follows: to provide a tracheostomy tube with integrated conductive regions which can be used to deliver bactericidal stimulation, a flexible lining for a mouth guard bath with integrated electrodes that can be activated to deliver bactericidal stimulation while the fixture is being cleaned.

One skilled in the art can appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specification, and following claims.

What is claimed is:

1. A device for remote monitoring of a wound or wound infection and treatment of the wound, the device comprising:
   a flexible and customized Integrated Surface Stimulation Device (ISSD) patch with electrodes, at least one temperature sensor, and a substrate, wherein at least a portion of the electrodes of said customized ISSD patch are configured to measure at least one wound impedance value associated with said wound or wound infection, wherein the at least one temperature sensor is configured to measure at least one wound temperature associated with the wound;
   an encapsulated power and control module electrically connected to said electrodes and said at least one temperature sensor of said customized ISSD patch, wherein said encapsulated power and control module is configured to control delivery of electrical stimulation to said wound or wound infection by said electrodes of said customized ISSD patch; and
   a remote control module having a bidirectional wireless communication module, said remote control module being in remote communication with said encapsulated power and control module wherein:
   said remote control module is configured to receive first and second outputs from said encapsulated power and control module, said first output being indicative of said at least one wound impedance value and said second output being indicative of said of said at least one wound temperature;
   said remote control module is configured to determine an infection status of the wound and a healing status of the wound based upon said first and second outputs received from the encapsulated power and control module; and
   said remote control module is configured to determine and execute a variable Electrical Stimulation (ES) profile through communication with said encapsulated power and control module, said electrodes of said customized ISSD patch being configured to deliver electrical stimulation in accordance with the ES profile, said remote control module being further configured to adjust the ES profile in real time based upon said first and second outputs received from the encapsulated power and control module.

2. The device according to claim 1, wherein said remote control module is configured to determine the infection status of said wound based upon said at least one temperature value.

3. The device according to claim 2, wherein said remote control module is configured to determine changes in said wound temperature, wherein said changes in wound temperature are indicative of the healing status of the wound.

4. The device according to claim 2, wherein said remote control module is configured to determine an increase in said wound temperature, wherein said increase in wound temperature is indicative of infection of said wound.

5. The device according to claim 1, wherein said electrodes of said ISSD patch are fabricated on said substrate.

6. The device according to claim 5, further comprising electrical interconnects that are fabricated on said substrate to electrically connect said electrodes of said ISSD patch with said encapsulated power and control module.

7. The device according to claim 1, wherein said substrate is disposable.

8. The device according to claim 1, wherein said encapsulated power and control module is completely encapsulated, and wherein said complete encapsulation is configured to seal off electronics of the power and control module.

9. The device according to claim 1, further comprising at least one power source electrically connected to said encapsulated power and control module and to said electrodes of said ISSD patch.

10. The device according to claim 1, wherein said remote control module is configured to determine the healing status of said wound based upon said at least one impedance value, and wherein an increase in impedance associated with said wound or infection is indicative of progressive said wound.

11. The device according to claim 1, wherein said encapsulated power and control module comprises first and second circuits that are configured to respectively determine said infection status and said healing status of said wound.

12. The device according to claim 1, wherein said remote control module comprises software that, when executed, is configured to determine said infection status and said healing status of said wound.

* * * * *